(12) United States Patent
Yu et al.

(10) Patent No.: US 11,367,185 B2
(45) Date of Patent: Jun. 21, 2022

(54) DEEP LEARNING-BASED MEDICAL IMAGE QUALITY EVALUATION AND VIRTUAL CLINICAL TRIAL

(71) Applicant: Mayo Foundation for Medical Education and Research, Rochester, MN (US)

(72) Inventors: Lifeng Yu, Byron, MN (US); Hao Gong, Rochester, MN (US); Shuai Leng, Rochester, MN (US); Cynthia H. McCollough, Byron, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 192 days.

(21) Appl. No.: 16/927,598

(22) Filed: Jul. 13, 2020

(65) Prior Publication Data
US 2021/0012487 A1   Jan. 14, 2021

Related U.S. Application Data

(60) Provisional application No. 62/873,542, filed on Jul. 12, 2019.

(51) Int. Cl.
| | |
|---|---|
| *G16H 30/40* | (2018.01) |
| *G16H 15/00* | (2018.01) |
| *G06T 7/00* | (2017.01) |
| *G16H 50/20* | (2018.01) |

(52) U.S. Cl.
CPC ........... *G06T 7/0012* (2013.01); *G16H 15/00* (2018.01); *G16H 30/40* (2018.01); *G16H 50/20* (2018.01); *G06T 2207/10081* (2013.01); *G06T 2207/20081* (2013.01); *G06T 2207/20084* (2013.01); *G06T 2207/20221* (2013.01); *G06T 2207/30096* (2013.01); *G06T 2207/30108* (2013.01)

(58) Field of Classification Search
CPC ......... G06T 7/0012; G06T 2207/10081; G06T 2207/20081; G06T 2207/20084; G06T 2207/20221; G06T 2207/30096; G06T 2207/30108; G06T 2207/30168; G16H 15/00; G16H 30/40; G16H 50/20; G16H 40/40
See application file for complete search history.

(56) References Cited

U.S. PATENT DOCUMENTS

| | | | |
|---|---|---|---|
| 10,610,182 B2* | 4/2020 | Suzuki | G06T 7/0014 |
| 2013/0202079 A1* | 8/2013 | Yu | A61B 6/5205 378/19 |
| 2020/0126271 A1* | 4/2020 | Liang | G06T 7/11 |

OTHER PUBLICATIONS

AAPM. Low Dose CT Grand Challenge. Accessed online at https://www.aapm.org/grandchallenge/lowdoseCT/. Version dated Jan. 7, 2019.

(Continued)

*Primary Examiner* — Siamak Harandi
(74) *Attorney, Agent, or Firm* — Quarles & Brady LLP

(57) ABSTRACT

A fully image-based framework for CT image, or other medical image, quality evaluation and virtual clinical trial using deep-learning techniques is provided. This framework includes deep learning-based noise insertion, lesion insertion, and model observer, which enable efficient, objective, and quantitative image quality evaluation and virtual clinical trial directly performed on patient images.

24 Claims, 10 Drawing Sheets

(56) References Cited

OTHER PUBLICATIONS

Alnowami, M, et al, "A deep learning model observer for use in alterative forced choice virtual clinical trials," Proc. SPIE 10577, Medical Imaging 2018: Image Perception, Observer Performance, and Technology Assessment, 105770Q (Mar. 7, 2018).

Ba, A., et al., Inter-laboratory comparison of channelized hotelling observer computation. Med Phys, 2018. 45(7): p. 3019-3030.

Chen, B., et al., Lesion insertion in the projection domain: Methods and initial results. Medical physics, 2015. 42(12): p. 7034-42.

Fessler, J.A. et al. Spatial resolution properties of penalized-likelihood image reconstruction: Space-invariant tomographs. Ieee Transactions on Image Processing, 1996. 5(9): p. 1346-1358.

Fletcher, J.G., et al., Estimation of Observer Performance for Reduced Radiation Dose Levels in CT: Eliminating Reduced Dose Levels That Are Too Low Is the First Step. Acad Radiol, 2017. 24(7): p. 876-890.

Fletcher, J.G., et al., Observer Performance with Varying Radiation Dose and Reconstruction Methods for Detection of Hepatic Metastases. Radiology, 2018. 289(2): p. 455-464.

Gang, G.J., et al., Task-based detectability in CT image reconstruction by filtered backprojection and penalized likelihood estimation. Medical Physics, 2014. 41(8): p. 081902.

Gong, H., et al. "A deep learning-and partial least square regression-based model observer for a low-contrast lesion detection task in CT." Medical physics 46.5 (2019): 2052-2063.

Leng, S., et al., Correlation between model observer and human observer performance in CT imaging when lesion location is uncertain. Med Phys, 2013. 40(8).

Pezeshk, A., et al. "Seamless lesion insertion for data augmentation in CAD training." IEEE transactions on medical imaging 36.4 (2016): 1005-1015.

Solomon, J., et al. Characteristic image quality of a third generation dualsource MDCT scanner: Noise, resolution, and detectability. Medical physics, 2015. 42(8): p. 4941-53.

Yu, L., et al., A virtual clinical trial using projection-based nodule insertion to determine radiologist reader performance in lung cancer screening CT. Proceedings of SPIE—the International Society for Optical Engineering, 2017. 10132.

Yu, L., et al., Development and validation of a practical lower-dose-simulation tool for optimizing Computed Tomography scan protocols. J Comput Assist Tomogr, 2012. 36(4): p. 477-488.

Yu, L., et al., Prediction of human observer performance in a 2-alternative forced choice lowcontrast detection task using channelized Hotelling observer: Impact of radiation dose and reconstruction algorithms. Med Phys, 2013. 40(4): p. 041908-1-9.

Yu, L., et al., Technical Note: Measuring contrast- and noise-dependent spatial resolution of an iterative reconstruction method in CT using ensemble averaging. Medical physics, 2015. 42(5): p. 2261-7.

Zhang, Y., et al., Correlation between human and model observer performance for discrimination task in CT. Physics in Medicine and Biology, 2014. 59(13): p. 3389-3404.

\* cited by examiner

DEEP LEARNING-BASED MEDICAL IMAGE QUALITY EVALUATION AND VIRTUAL CLINICAL TRIAL

CROSS-REFERENCE TO RELATED APPLICATIONS

This application claims the benefit of U.S. Provisional Patent Application Ser. No. 62/873,542, filed on Jul. 12, 2019, and entitled "DEEP LEARNING-BASED MEDICAL IMAGE QUALITY EVALUATION AND VIRTUAL CLINICAL TRIAL," which is herein incorporated by reference in its entirety.

STATEMENT REGARDING FEDERALLY SPONSORED RESEARCH

This invention was made with government support under EB017095 awarded by the National Institutes of Health. The government has certain rights in the invention.

BACKGROUND

Objective and quantitative image quality evaluation is important for system optimization and radiation dose reduction in CT. It is important to maintain the desired diagnostic image quality while reducing radiation dose or making any changes in CT system hardware and software. Many image quality evaluation approaches have been proposed. Traditional methods that have been widely used involve measurement of modulation transfer function ("MTF"), slice sensitivity profile ("SSP"), noise power spectrum ("NPS"), and contrast-to-noise ratio ("CNR"). It has been demonstrated that these metrics have major limitations when non-linear reconstruction and noise reduction methods are used to generate the images.

Task-based image quality metrics using mathematical model observers, either frequency-based or image-based, have been studied extensively in recent years. Strong correlation of performance between channelized Hotelling observer ("CHO") and human observers have been demonstrated in some phantom based detection, classification, and localization tasks. However, it remains challenging to generalize these approaches to realistic diagnostic tasks involving patient anatomical background.

In addition, simulating lower-dose exams from existing routine-dose exams and inserting lesions to existing images have been proved to be powerful tools for CT image quality evaluation and virtual clinical trial. These tools have been used in multiple large-scale radiologist observer studies for radiation dose optimization and performance evaluation. However, most of these tools are operated in the projection data domain, and therefore have limited applicability due to the lack of access to the patient raw data and because the data processing is tedious and cumbersome.

SUMMARY OF THE DISCLOSURE

The present disclosure addresses the aforementioned drawbacks by providing a method for generating a report indicating diagnostic performance of a computed tomography (CT) system. CT images acquired from a subject using a CT system are accessed. The CT images depict anatomy of the subject. Lesion-present images are generated by inserting lesion data to the CT images, the lesion-present images depicting lesions added to the anatomy of the subject. Lower-dose CT images are generated by inserting noise to the CT images and the lesion-present images, the lower-dose CT images corresponding to lower dose representations of the CT images and lesion-present images. One or more measures of diagnostic performance of the CT system are generated by inputting input image data comprising the CT images, lesion-present images, and lower-dose CT images to a deep learning-based model observer, generating output as the one or more measures of diagnostic performance. A report of diagnostic performance of the CT system is then generated based on the one or more measures of diagnostic performance of the CT system.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for a fully image-based framework for CT image, or other medical image, quality evaluation and virtual clinical trial using deep-learning techniques. This framework includes deep learning-based noise insertion, lesion insertion, and model observer, which enable efficient, objective, and quantitative image quality evaluation and virtual clinical trial directly performed on patient images.

The proposed framework includes at least three components: a Deep-Learning Noise Insertion (DL-NI) tool, a Deep-Learning Lesion Insertion (DL-LI) tool, and a Deep-Learning Model Observer (DL-MO) tool, as shown in FIG.

1. The three components can be used in combination or individually, depending on the particular evaluation tasks at hand.

Figure 1:
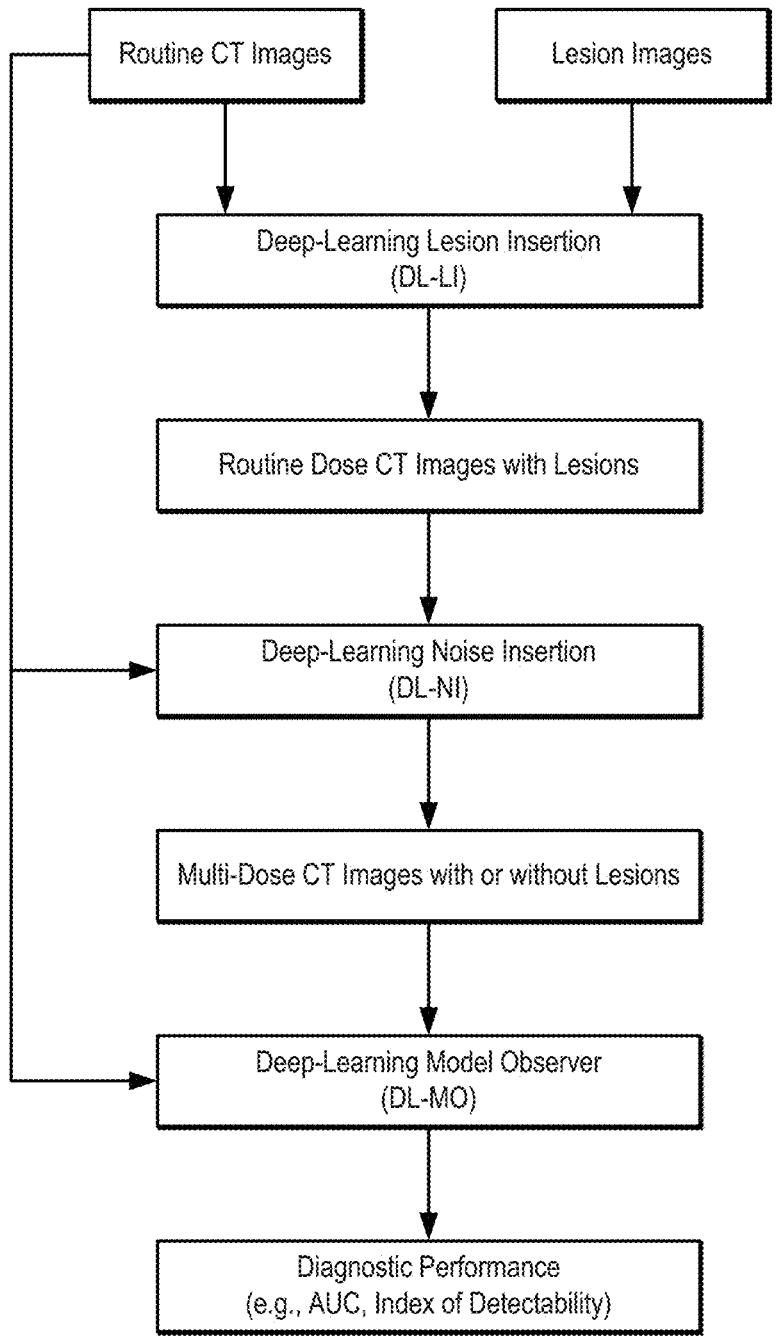
FIG. 1 is a flowchart setting forth the general workflow for a deep-learning-based medical image quality evaluation and virtual clinical trial system.

As shown in FIG. 1, the systems and methods for image quality evaluation and virtual clinical trial can include inputting routine CT image, or other medical images, and lesion-present images (i.e., medical images containing lesion or simulated lesion) to one or more of a DL-LI system, a DL-NI system, and a DL-MO system.

The routine CT images and lesion data can be input to the DL-LI system, generating output as routine dose CT images containing lesions (i.e., lesion-present images). The lesion data may include, for instance, patient lesion model data. Additionally or alternatively, routine dose CT images containing lesions can be generated using other lesion insertion techniques, including projection domain-based lesion insertion methods.

The routine CT images and routine CT images containing lesions can also be input to a DL-NI system, generating output as multiple lower-dose CT images with or without lesions. Additionally or alternatively, the multiple lower-dose CT images can be generated using other noise insertion methods, such as projection domain-based noise insertion methods.

The routine CT images and multiple lower-dose CT images (both with or without lesions) are input to a DL-MO system, generating output as a report indicating diagnostic performance, which may include an evaluation of image quality, virtual clinical trial, or both. The report may include or otherwise indicate an area under the curve ("AUC") metric, an index of detectability, other figure-of-merit, or combinations thereof. As noted above, the multiple lower-dose CT images can be generated using the DL-LI systems and methods, DL-NI systems and methods, or other suitable lesion insertion and noise insertion techniques.

It is one aspect of the disclosure to provide a deep learning-based noise insertion system and method that is capable of simulating realistic lower-dose patient CT exams directly in image domain, which is more efficient and convenient than conventional projection-domain approaches.

The conventional projection-domain based low-dose CT exam simulation requires access to the projection data and vendor-specific proprietary information that is not readily available. Projection-domain based methods are also usually time-consuming, as they involves projection data modification and image reconstruction. The conventional image-domain based method cannot yield realistic low-dose images. On the contrary, the proposed DL-NI method can directly perform on reconstructed CT images from different CT systems and institutions, with realistic image texture and much higher computational efficiency.

Figure 2:
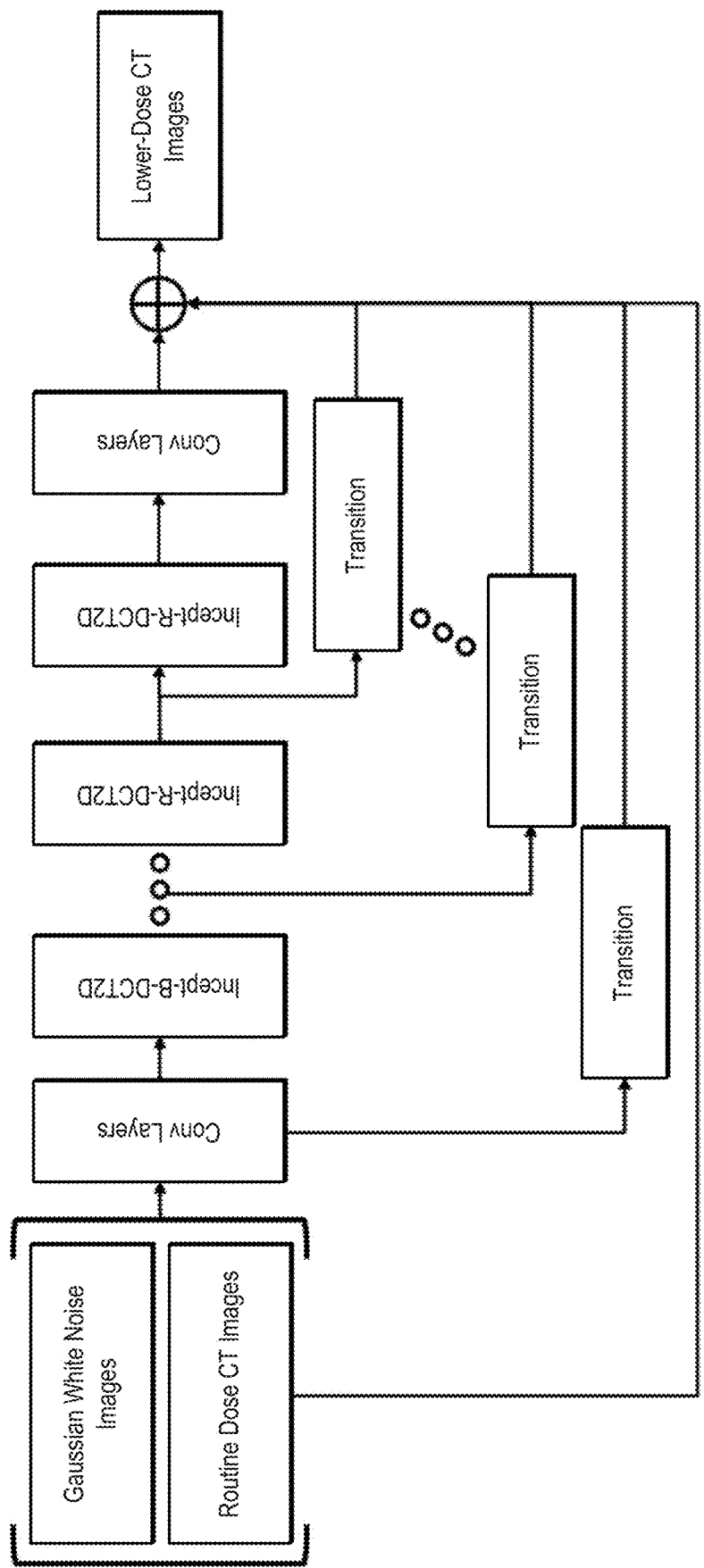
FIG. 2 is a flowchart setting forth the general workflow for a deep-learning-based noise insertion system, which implements a perceptual loss, spectral loss, and diversity loss function.

As one example the DL-NI systems and methods can be based on a deep convolutional neural network ("CNN") architecture, such as the one shown in FIG. 2. The design of the network architecture can implement a generalized mathematical model that enables the synthesis of lower-dose CT images, using routine-dose CT images and noise (e.g., Gaussian white noise) as the inputs. The objective function of the CNN jointly minimizes three customized loss functions: a perceptual loss function to achieve perceptually-realistic low-dose CT images, a frequency-spectrum loss to quantitatively match the noise frequency components, and a diversity loss to ensure sufficient diversity of noise realization. In some implementations, a hybrid of local and non-local operators can be used to model noise correlation in the CT images. In the example shown in FIG. 2, the deep CNN architecture implemented for the DL-NI includes incept-B-DCT2D and incept-R-DCT2D functional modules. These functional modules are configured to concatenate non-local operators and multi-scale local convolutional operators to model noise correlation in CT images. In some implementations, the non-local operators can be two-dimensional discrete cosine transformations.

Figure 3:
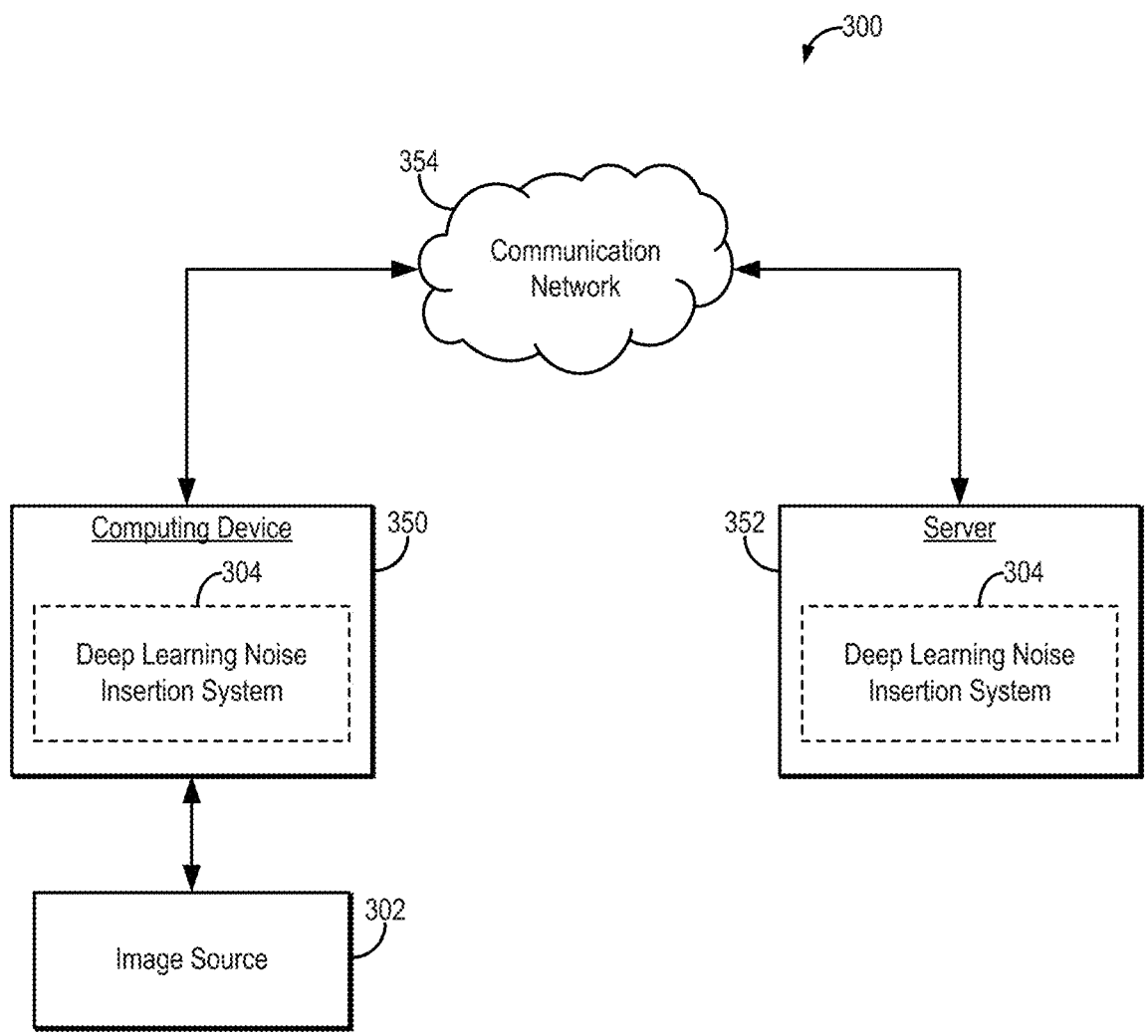
FIG. 3 is a block diagram of an example deep learning noise insertion system.

Referring now to FIG. 3, an example of a system 300 for deep learning-based noise insertion in medical images in accordance with some embodiments of the systems and methods described in the present disclosure is shown. As shown in FIG. 3, a computing device 350 can receive one or more types of data (e.g., CT image data) from image source 302, which may be a CT image source or other suitable medical image source. In some embodiments, computing device 350 can execute at least a portion of a deep learning noise insertion system 304 to generate simulated lower dose images from data received from the image source 302.

Additionally or alternatively, in some embodiments, the computing device 350 can communicate information about data received from the image source 302 to a server 352 over a communication network 354, which can execute at least a portion of the deep learning noise insertion system 304. In such embodiments, the server 352 can return information to the computing device 350 (and/or any other suitable computing device) indicative of an output of the deep learning noise insertion system 304.

In some embodiments, computing device 350 and/or server 352 can be any suitable computing device or combination of devices, such as a desktop computer, a laptop computer, a smartphone, a tablet computer, a wearable computer, a server computer, a virtual machine being executed by a physical computing device, and so on. The computing device 350 and/or server 352 can also reconstruct images from the data.

In some embodiments, image source 302 can be any suitable source of image data (e.g., measurement data, images reconstructed from measurement data), such as a CT system (or other suitable medical imaging system), another computing device (e.g., a server storing image data), and so on. In some embodiments, image source 302 can be local to computing device 350. For example, image source 302 can be incorporated with computing device 350 (e.g., computing device 350 can be configured as part of a device for capturing, scanning, and/or storing images). As another example, image source 302 can be connected to computing device 350 by a cable, a direct wireless link, and so on. Additionally or alternatively, in some embodiments, image source 302 can be located locally and/or remotely from computing device 350, and can communicate data to computing device 350 (and/or server 352) via a communication network (e.g., communication network 354).

In some embodiments, communication network 354 can be any suitable communication network or combination of communication networks. For example, communication network 354 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 3 can each be any suitable communications link or combination of communications links, such as wired links, fiber optic links, Wi-Fi links, Bluetooth links, cellular links, and so on.

Figure 4:
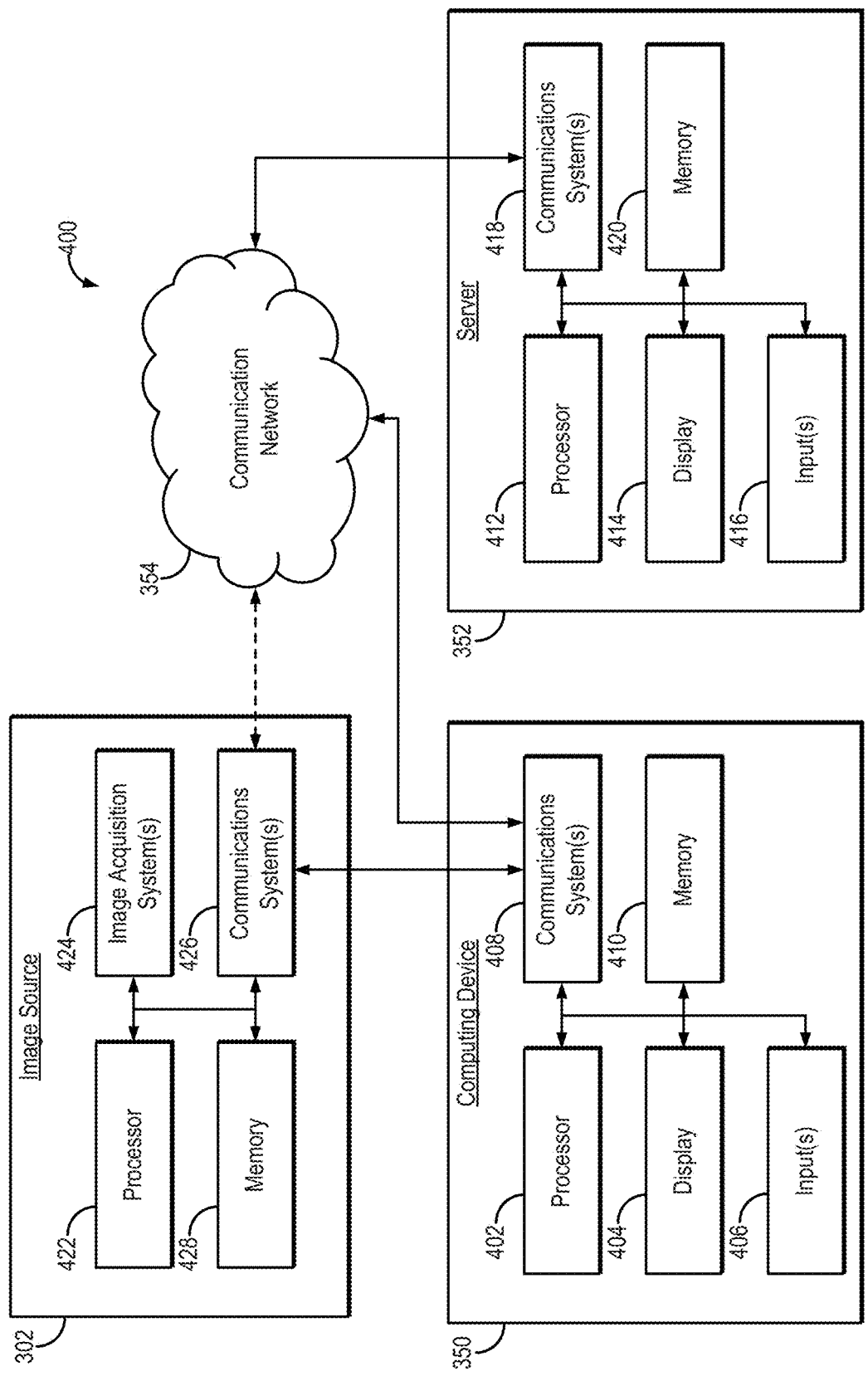
FIG. 4 is a block diagram of example components that can implement the deep learning noise insertion system of FIG. 3.

Referring now to FIG. 4, an example of hardware 400 that can be used to implement image source 302, computing device 350, and server 352 in accordance with some embodiments of the systems and methods described in the present disclosure is shown. As shown in FIG. 4, in some embodiments, computing device 350 can include a processor 402, a display 404, one or more inputs 406, one or more communication systems 408, and/or memory 410. In some embodiments, processor 402 can be any suitable hardware processor or combination of processors, such as a central processing unit ("CPU"), a graphics processing unit ("GPU"), and so on. In some embodiments, display 404 can include any suitable display devices, such as a computer monitor, a touchscreen, a television, and so on. In some embodiments, inputs 406 can include any suitable input devices and/or sensors that can be used to receive user input, such as a keyboard, a mouse, a touchscreen, a microphone, and so on.

In some embodiments, communications systems 408 can include any suitable hardware, firmware, and/or software for communicating information over communication network 354 and/or any other suitable communication networks. For example, communications systems 408 can include one or more transceivers, one or more communication chips and/or chip sets, and so on. In a more particular example, communications systems 408 can include hardware, firmware and/or software that can be used to establish a Wi-Fi connection, a Bluetooth connection, a cellular connection, an Ethernet connection, and so on.

In some embodiments, memory 410 can include any suitable storage device or devices that can be used to store instructions, values, data, or the like, that can be used, for example, by processor 402 to present content using display 404, to communicate with server 352 via communications system(s) 408, and so on. Memory 410 can include any suitable volatile memory, non-volatile memory, storage, or any suitable combination thereof. For example, memory 410 can include RAM, ROM, EEPROM, one or more flash drives, one or more hard disks, one or more solid state drives, one or more optical drives, and so on. In some embodiments, memory 410 can have encoded thereon, or otherwise stored therein, a computer program for controlling operation of computing device 350. In such embodiments, processor 402 can execute at least a portion of the computer program to present content (e.g., images, user interfaces, graphics, tables), receive content from server 352, transmit information to server 352, and so on.

In some embodiments, server 352 can include a processor 412, a display 414, one or more inputs 416, one or more communications systems 418, and/or memory 420. In some embodiments, processor 412 can be any suitable hardware processor or combination of processors, such as a CPU, a GPU, and so on. In some embodiments, display 414 can include any suitable display devices, such as a computer monitor, a touchscreen, a television, and so on. In some embodiments, inputs 416 can include any suitable input devices and/or sensors that can be used to receive user input, such as a keyboard, a mouse, a touchscreen, a microphone, and so on.

In some embodiments, communications systems 418 can include any suitable hardware, firmware, and/or software for communicating information over communication network 354 and/or any other suitable communication networks. For example, communications systems 418 can include one or more transceivers, one or more communication chips and/or chip sets, and so on. In a more particular example, communications systems 418 can include hardware, firmware and/or software that can be used to establish a Wi-Fi connection, a Bluetooth connection, a cellular connection, an Ethernet connection, and so on.

In some embodiments, memory 420 can include any suitable storage device or devices that can be used to store instructions, values, data, or the like, that can be used, for example, by processor 412 to present content using display 414, to communicate with one or more computing devices 350, and so on. Memory 420 can include any suitable volatile memory, non-volatile memory, storage, or any suitable combination thereof. For example, memory 420 can include RAM, ROM, EEPROM, one or more flash drives, one or more hard disks, one or more solid state drives, one or more optical drives, and so on. In some embodiments, memory 420 can have encoded thereon a server program for controlling operation of server 352. In such embodiments, processor 412 can execute at least a portion of the server program to transmit information and/or content (e.g., data, images, a user interface) to one or more computing devices 350, receive information and/or content from one or more computing devices 350, receive instructions from one or more devices (e.g., a personal computer, a laptop computer, a tablet computer, a smartphone), and so on.

In some embodiments, image source 302 can include a processor 422, one or more image acquisition systems 424, one or more communications systems 426, and/or memory 428. In some embodiments, processor 422 can be any suitable hardware processor or combination of processors, such as a CPU, a GPU, and so on. In some embodiments, the one or more image acquisition systems 424 are generally configured to acquire data, images, or both, and can include a CT system or other suitable medical imaging system. Additionally or alternatively, in some embodiments, one or more image acquisition systems 424 can include any suitable hardware, firmware, and/or software for coupling to and/or controlling operations of a CT system or other suitable medical imaging system. In some embodiments, one or more portions of the one or more image acquisition systems 424 can be removable and/or replaceable.

Note that, although not shown, image source 302 can include any suitable inputs and/or outputs. For example, image source 302 can include input devices and/or sensors that can be used to receive user input, such as a keyboard, a mouse, a touchscreen, a microphone, a trackpad, a trackball, and so on. As another example, image source 302 can include any suitable display devices, such as a computer monitor, a touchscreen, a television, etc., one or more speakers, and so on.

In some embodiments, communications systems 426 can include any suitable hardware, firmware, and/or software for communicating information to computing device 350 (and, in some embodiments, over communication network 354 and/or any other suitable communication networks). For example, communications systems 426 can include one or more transceivers, one or more communication chips and/or chip sets, and so on. In a more particular example, communications systems 426 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 428 can include any suitable storage device or devices that can be used to store instructions, values, data, or the like, that can be used, for example, by processor 422 to control the one or more image acquisition systems 424, and/or receive data from the one or more image acquisition systems 424; to images from data; present content (e.g., images, a user interface) using a display; communicate with one or more computing devices 350; and so on. Memory 428 can include any suitable volatile memory, non-volatile memory, storage, or any suitable combination thereof. For example, memory 428 can include RAM, ROM, EEPROM, one or more flash drives, one or more hard disks, one or more solid state drives, one or more optical drives, and so on. In some embodiments, memory 428 can have encoded thereon, or otherwise stored therein, a program for controlling operation of image source 302. In such embodiments, processor 422 can execute at least a portion of the program to generate images, transmit information and/or content (e.g., data, images) to one or more computing devices 350, receive information and/or content from one or more computing devices 350, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Figure 5:
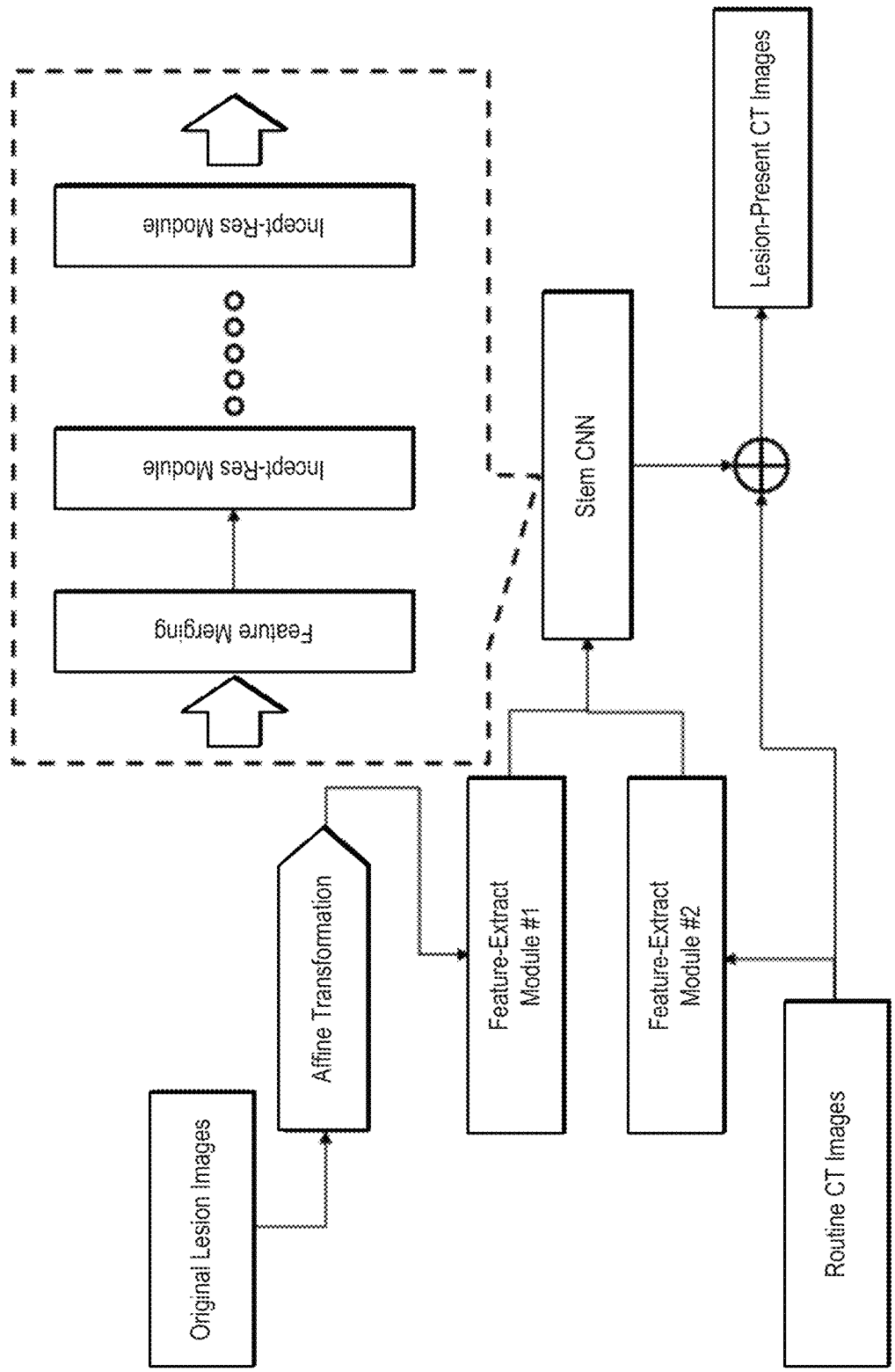
FIG. 5 is a flowchart setting forth the general workflow for a deep-learning-based lesion insertion system.

It is another aspect of the present disclosure to provide deep learning-based lesion insertion ("DL-LI") systems and methods. The DL-LI systems and methods are based on a deep CNN architecture, such as the one shown in FIG. 5. $CNN_{Lesion}$ inserts lesions into different locations of patient images by fusing multi-scaled features of patient lesion models with anatomical background.

In an example implementation, a cohort of lesion-free CT images was used to generate training data and validate $CNN_{Lesion}$. A previously-validated projection-based lesion insertion technique was used to generate reference images across ten conditions: lesion sizes 5-11 mm, contrast levels 15-25 HU, and reconstruction types (filtered-backprojection and iterative reconstruction).

The $CNN_{Lesion}$-synthesized lesion-present images showed strong perceptual similarity compared to the reference images. The mean structural similarity index and the mean absolute CT number difference between the $CNN_{Lesion}$-inserted lesions and the reference were 0.983±0.004 and 1.9±0.3 HU, respectively.

Figure 6:
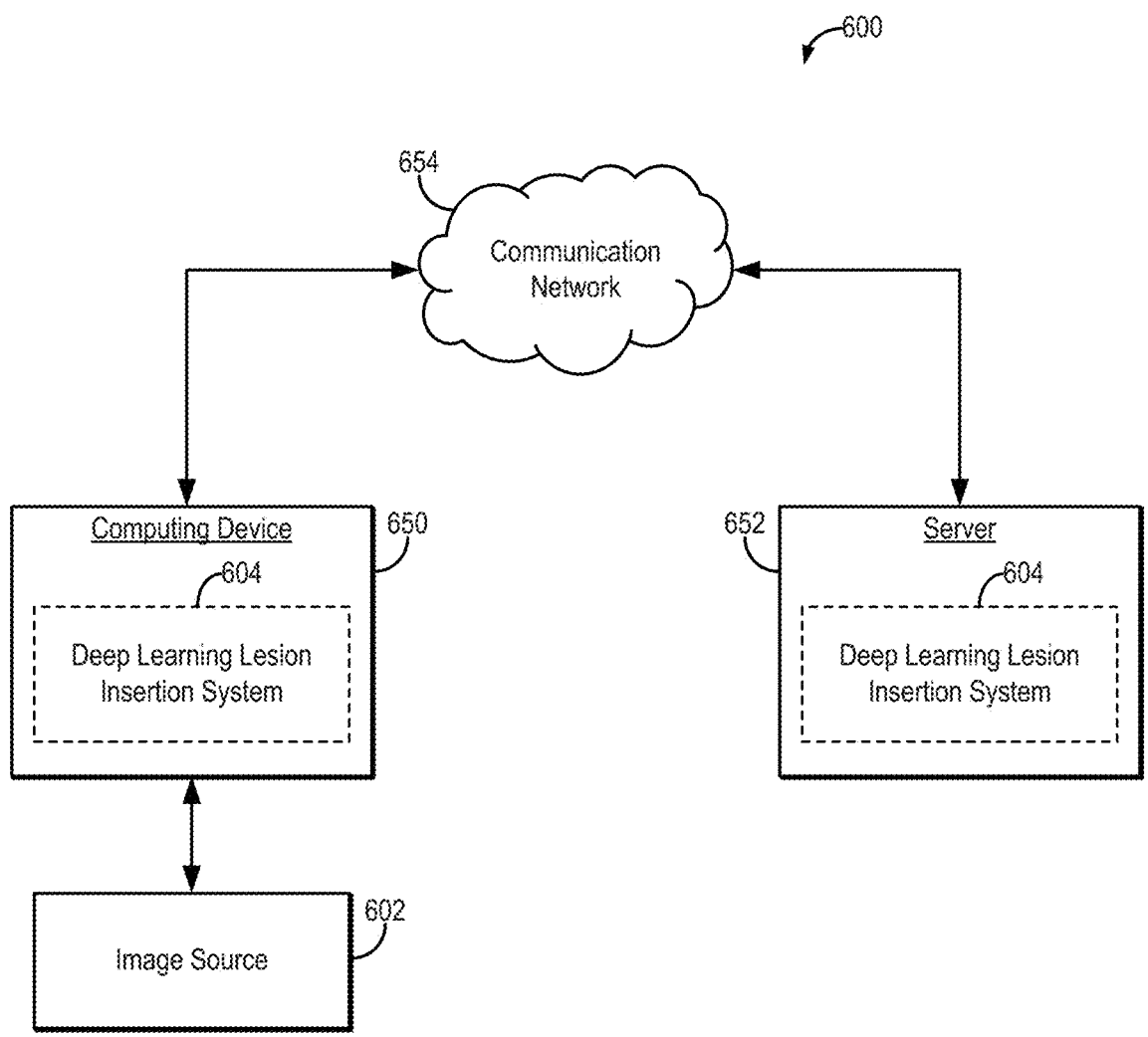
FIG. 6 is a block diagram of an example deep learning lesion insertion system.

Referring now to FIG. 6, an example of a system 600 for deep learning-based lesion insertion ("DL-LI") in medical images in accordance with some embodiments of the systems and methods described in the present disclosure is shown. As shown in FIG. 6, a computing device 650 can receive one or more types of data (e.g., CT image data) from image source 602, which may be a CT image source or other suitable medical image source. In some embodiments, computing device 650 can execute at least a portion of a deep learning lesion insertion system 604 to insert lesion into medical images from data received from the image source 602. For instance, the deep learning lesion insertion system 604 can generate lesion-present images in which simulated lesions have been added to medical images in the image domain.

Additionally or alternatively, in some embodiments, the computing device 650 can communicate information about data received from the image source 602 to a server 652 over a communication network 654, which can execute at least a portion of the deep learning lesion insertion system 604. In such embodiments, the server 652 can return information to the computing device 650 (and/or any other suitable computing device) indicative of an output of the deep learning lesion insertion system 604.

In some embodiments, computing device 650 and/or server 652 can be any suitable computing device or combination of devices, such as a desktop computer, a laptop computer, a smartphone, a tablet computer, a wearable computer, a server computer, a virtual machine being executed by a physical computing device, and so on. The computing device 650 and/or server 652 can also reconstruct images from the data.

In some embodiments, image source 602 can be any suitable source of image data (e.g., measurement data, images reconstructed from measurement data), such as a CT system (or other suitable medical imaging system), another computing device (e.g., a server storing image data), and so on. In some embodiments, image source 602 can be local to computing device 650. For example, image source 602 can be incorporated with computing device 650 (e.g., computing device 650 can be configured as part of a device for capturing, scanning, and/or storing images). As another example, image source 602 can be connected to computing device 650 by a cable, a direct wireless link, and so on. Additionally or alternatively, in some embodiments, image source 602 can be located locally and/or remotely from computing device 650, and can communicate data to computing device 650 (and/or server 652) via a communication network (e.g., communication network 654).

In some embodiments, communication network 654 can be any suitable communication network or combination of communication networks. For example, communication network 654 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 6 can each be any suitable communications link or combination of communications links, such as wired links, fiber optic links, Wi-Fi links, Bluetooth links, cellular links, and so on.

Figure 7:
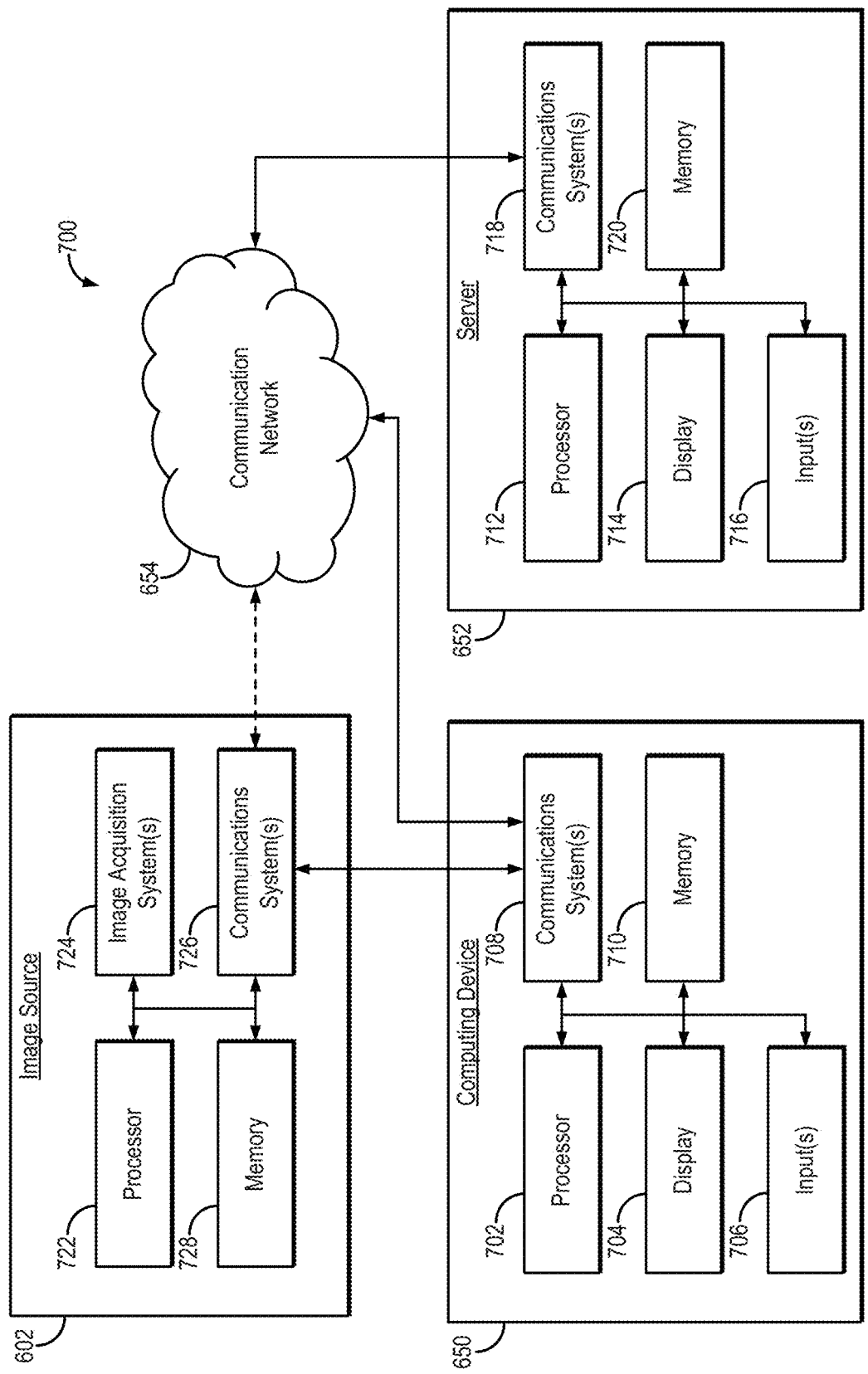
FIG. 7 is a block diagram of example components that can implement the deep learning lesion insertion system of FIG. 6.

Referring now to FIG. 7, an example of hardware 700 that can be used to implement image source 602, computing device 650, and server 652 in accordance with some embodiments of the systems and methods described in the present disclosure is shown. As shown in FIG. 7, in some embodiments, computing device 650 can include a processor 702, a display 704, one or more inputs 706, one or more communication systems 708, and/or memory 710. In some embodiments, processor 702 can be any suitable hardware processor or combination of processors, such as a central processing unit ("CPU"), a graphics processing unit ("GPU"), and so on. In some embodiments, display 704 can include any suitable display devices, such as a computer monitor, a touchscreen, a television, and so on. In some embodiments, inputs 706 can include any suitable input devices and/or sensors that can be used to receive user input, such as a keyboard, a mouse, a touchscreen, a microphone, and so on.

In some embodiments, communications systems 708 can include any suitable hardware, firmware, and/or software for communicating information over communication network 654 and/or any other suitable communication networks. For example, communications systems 708 can include one or more transceivers, one or more communication chips and/or chip sets, and so on. In a more particular example, communications systems 708 can include hardware, firmware and/or software that can be used to establish a Wi-Fi connection, a Bluetooth connection, a cellular connection, an Ethernet connection, and so on.

In some embodiments, memory 710 can include any suitable storage device or devices that can be used to store instructions, values, data, or the like, that can be used, for example, by processor 702 to present content using display 704, to communicate with server 652 via communications system(s) 708, and so on. Memory 710 can include any suitable volatile memory, non-volatile memory, storage, or any suitable combination thereof. For example, memory 710 can include RAM, ROM, EEPROM, one or more flash drives, one or more hard disks, one or more solid state drives, one or more optical drives, and so on. In some embodiments, memory 710 can have encoded thereon, or otherwise stored therein, a computer program for controlling operation of computing device 650. In such embodiments, processor 702 can execute at least a portion of the computer program to present content (e.g., images, user interfaces, graphics, tables), receive content from server 652, transmit information to server 652, and so on.

In some embodiments, server 652 can include a processor 712, a display 714, one or more inputs 716, one or more communications systems 718, and/or memory 720. In some embodiments, processor 712 can be any suitable hardware processor or combination of processors, such as a CPU, a GPU, and so on. In some embodiments, display 714 can include any suitable display devices, such as a computer monitor, a touchscreen, a television, and so on. In some embodiments, inputs 716 can include any suitable input devices and/or sensors that can be used to receive user input, such as a keyboard, a mouse, a touchscreen, a microphone, and so on.

In some embodiments, communications systems 718 can include any suitable hardware, firmware, and/or software for communicating information over communication network 654 and/or any other suitable communication networks. For example, communications systems 718 can include one or more transceivers, one or more communication chips and/or chip sets, and so on. In a more particular example, communications systems 718 can include hardware, firmware and/or software that can be used to establish a Wi-Fi connection, a Bluetooth connection, a cellular connection, an Ethernet connection, and so on.

In some embodiments, memory 720 can include any suitable storage device or devices that can be used to store instructions, values, data, or the like, that can be used, for example, by processor 712 to present content using display 714, to communicate with one or more computing devices 650, and so on. Memory 720 can include any suitable volatile memory, non-volatile memory, storage, or any suitable combination thereof. For example, memory 720 can include RAM, ROM, EEPROM, one or more flash drives, one or more hard disks, one or more solid state drives, one or more optical drives, and so on. In some embodiments, memory 720 can have encoded thereon a server program for controlling operation of server 652. In such embodiments, processor 712 can execute at least a portion of the server program to transmit information and/or content (e.g., data, images, a user interface) to one or more computing devices 650, receive information and/or content from one or more computing devices 650, receive instructions from one or more devices (e.g., a personal computer, a laptop computer, a tablet computer, a smartphone), and so on.

In some embodiments, image source 602 can include a processor 722, one or more image acquisition systems 724, one or more communications systems 726, and/or memory 728. In some embodiments, processor 722 can be any suitable hardware processor or combination of processors, such as a CPU, a GPU, and so on. In some embodiments, the one or more image acquisition systems 724 are generally configured to acquire data, images, or both, and can include a CT system or other suitable medical imaging system. Additionally or alternatively, in some embodiments, one or more image acquisition systems 724 can include any suitable hardware, firmware, and/or software for coupling to and/or controlling operations of a CT system or other suitable medical imaging system. In some embodiments, one or more portions of the one or more image acquisition systems 724 can be removable and/or replaceable.

Note that, although not shown, image source 602 can include any suitable inputs and/or outputs. For example, image source 602 can include input devices and/or sensors that can be used to receive user input, such as a keyboard, a mouse, a touchscreen, a microphone, a trackpad, a trackball, and so on. As another example, image source 602 can include any suitable display devices, such as a computer monitor, a touchscreen, a television, etc., one or more speakers, and so on.

In some embodiments, communications systems 726 can include any suitable hardware, firmware, and/or software for communicating information to computing device 650 (and, in some embodiments, over communication network 654 and/or any other suitable communication networks). For example, communications systems 726 can include one or more transceivers, one or more communication chips and/or chip sets, and so on. In a more particular example, communications systems 726 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 728 can include any suitable storage device or devices that can be used to store instructions, values, data, or the like, that can be used, for example, by processor 722 to control the one or more image acquisition systems 724, and/or receive data from the one or more image acquisition systems 724; to images from data; present content (e.g., images, a user interface) using a display; communicate with one or more computing devices 650; and so on. Memory 728 can include any suitable volatile memory, non-volatile memory, storage, or any suitable combination thereof. For example, memory 728 can include RAM, ROM, EEPROM, one or more flash drives, one or more hard disks, one or more solid state drives, one or more optical drives, and so on. In some embodiments, memory 728 can have encoded thereon, or otherwise stored therein, a program for controlling operation of image source 602. In such embodiments, processor 722 can execute at least a portion of the program to generate images, transmit information and/or content (e.g., data, images) to one or more computing devices 650, receive information and/or content from one or more computing devices 650, receive instructions from one or more devices (e.g., a personal computer, a laptop computer, a tablet computer, a smart-phone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Figure 8:
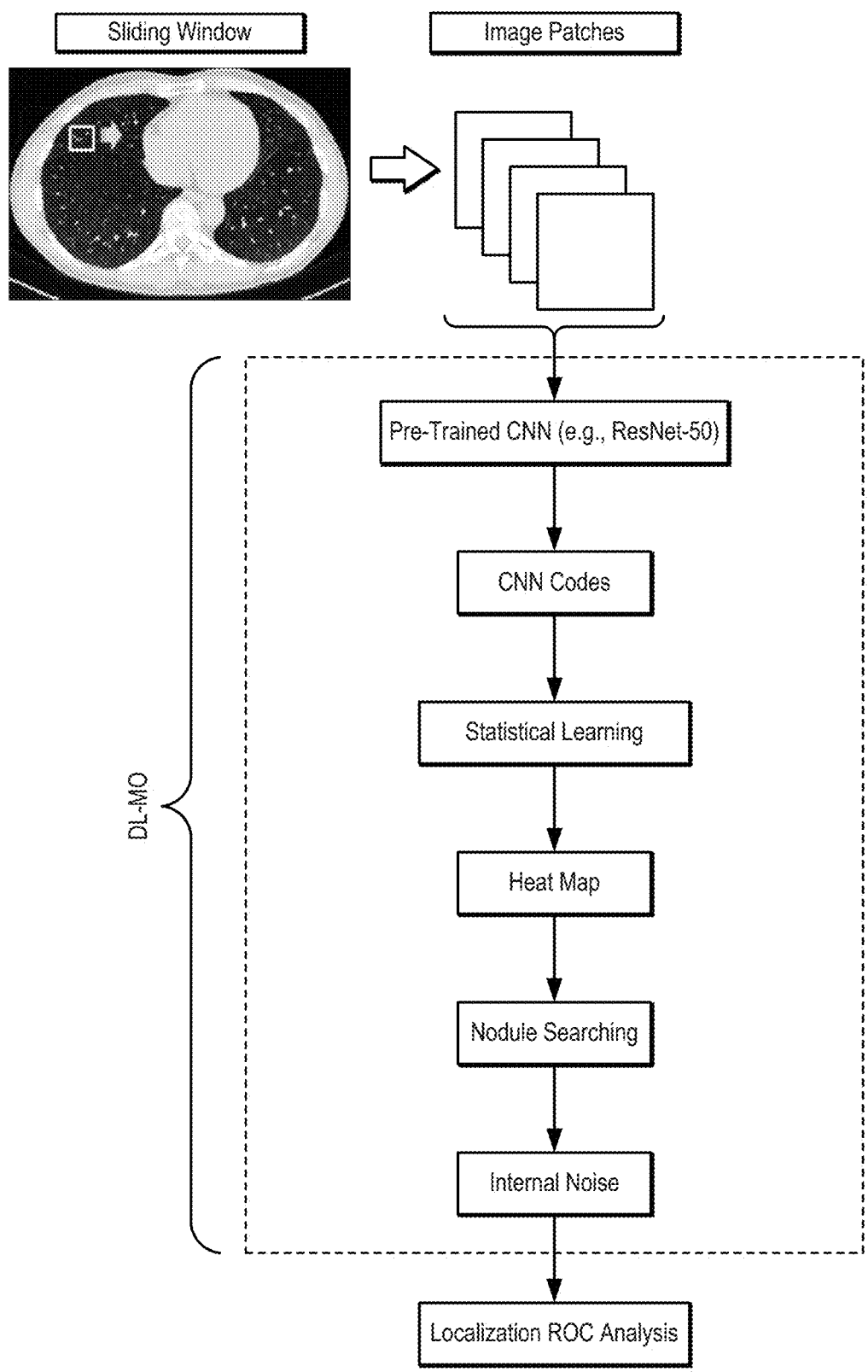
FIG. 8 is a schematic illustration of the framework of an example deep-learning-based model observer for a localization task, which includes a pre-trained convolutional neural network, a partial-least-square regression model, a nodule searching process, and an internal noise component.

It is another aspect of the present disclosure to provide deep learning-based model observer ("DL-MO") systems and methods. The generic framework of an example DL-MO is illustrated in FIG. 8. Briefly, the DL-MO includes at least three components: a pre-trained deep convolutional neural network (DCNN), a feature-engineering model, and an internal noise component, examples of which are described below in more detail.

As an example, the DCNN can be a ResNet-50 that was pre-trained on a natural image database (e.g., ImageNet). Raw feature maps (termed as "CNN codes") of the input CT images can be extracted from an intermediate layer of the DCNN. A partial-least-square regression can be used as the feature-engineering model to further augment the CNN codes and generate the test statistics $\lambda_0$ without the internal noise. Then, the internal noise component can be added to $\lambda_0$ to model HO performance variability: $\lambda = \lambda_0 + \alpha \cdot x$, where $\lambda$ is the final test statistics of DL-MO, $\alpha$ is the weighting factor, $x$ is a Gaussian random variable with a zero expectation and the same standard deviation as the test statistics of nodule-absent images.

As one non-limiting example, the DL-MO can be constructed using a transfer learning strategy, in which the knowledge gained while solving one task is applied to address a different, but relevant, task. Briefly, transfer learning adapts any prior machine learning model (e.g., CNN) pre-trained for a pair of source domain, $D_S$, and source task, $T_S$, to another pair of target domain, $D_T$, and target task $T_T$. The prior model defines a functional mapping from the source domain to the source task. Then, the prior model is adapted to generate a new mapping from the target domain to the target task.

Assuming the similarity between the source domain and the target domain, the prior model can be used as a fixed feature extractor to generate new features X' (i.e., the intrinsic features that are explored and exploited by the prior model from the input images) on the target domain, and a secondary model (e.g., statistical model) can be trained over X' for the target task. The degree of similarity between the source domain and target domain can be evaluated in terms of the image content (e.g., the object types) and the image features that may be relevant to the source/target tasks.

As one non-limiting example, when the prior model is a CNN, the feature (also termed as CNN codes) can be directly extracted from any intermediate layer in the network architecture. The selection of CNN layer often follows a generic guideline, that is, the earlier layers are likely to provide domain-invariant feature, while the later layers tend to generate domain-specific feature. As noted above, as a non-limiting example a 50-layer Residual net (ResNet-50) can be used as the prior model. The ResNet-50 can be pre-trained over a database of images (i.e., the source domain is the image domain), such as the ImageNet database. In some instances, ResNet can be interpreted as the encoder part of deep convolutional framelets, and thus, the corresponding CNN codes can be represented in the following matrix form:

$$X' = \phi \cdot \rho(H - p(H \cdot \psi) \cdot \overline{\psi}) \quad (1);$$

where H is the Hankel matrix of the input of the layer used for feature extraction, $\psi$ and $\overline{\psi}$ denote subsequent local bases (e.g., convolutional filters) in the same residual block (e.g., the building block in residual networks), $\rho$ is a ReLU (i.e., Rectified linear unit) or other suitable activation function, and $\phi$ denotes the non-local bases (e.g., pooling operator).

Eqn. (1) provides a mathematical representation of X' for the special case that the prior model is a residual network, and thus, the specific form of X' would vary if a different prior model is used. Furthermore, the local and non-local bases are redundant and non-orthonormal, which may result in inner correlation and high dimensionality of X'. Because inner correlation and high dimensionality could in some instances degrade the performance of the secondary model for the target task, the features X' can be further processed by one or more feature engineering methods.

As one non-limiting example, to construct the secondary model for the target task, a partial least squares discriminant analysis ("PLS-DA") model can be used. The PLS-DA model can incorporate model generation with an embedded feature engineering procedure that addresses the potential inner correlation and high dimensionality of X'.

In an example implementation, the input CNN codes X' are standardized and then represented as a linear form:

$$X' = V \cdot P + E \quad (2);$$

where V is the X-score matrix (i.e., each column is a PLS component), P is the predictor loading matrix, and E is the predictor residual. In this example, the target task can be considered as a binary classification task, and the ideal model response can be represented as a linear form:

$$C = U \cdot Q + F \quad (3);$$

where $C = \{C_k, k=1, 2, \ldots\}$ is the ideal model response for each sample of X', that is, C is a discrete label vector ($C_i = 1$ for the ith lesion-present case, and $C_j = -1$ for the jth lesion-absent case), U is the C-score matrix (i.e., the linear combination of the responses that has the maximal covariance with the PLS components), Q is the response loading matrix, and F is the response residual.

Based on the Eqns. (2) and (3), the loading matrices P and Q can be calculated by regressing X' and C across V and U, respectively. In some implementations, it can be assumed that there exists a linear inner relation U=V·D+F''', where D is a diagonal matrix and F''' is the residual. Furthermore, the X-score matrix V can be calculated as V=X'·W, where the weight matrix W is calculated in an iterative process that involves solving the eigenvectors for the successively deflated X'·C. Then, a prediction model can be created by calculating a regression coefficient vector B that mapped X' to C as follows:

$$C = U \cdot Q + F = X' \cdot B + F' \quad (4);$$

$$B = W \cdot D \cdot Q \quad (5).$$

When the residual terms F, F', and F''' are negligible, the model response C' (also denoted as PLS-DA model test statistics $\lambda_0$), for any new CNN codes $X_{new}'$ from unknown origin can be formulated as $C' = X_{new}' \cdot B$. Furthermore, C' is typically a set of continuous values, although the PLS-DA model was trained with the discrete label vector C. Thus, a decision threshold could be determined to classify the lesion-present/absent cases.

The use of internal noise was to model the inefficiency and variability of HO performance in lesion detection task. As one non-limiting example, the decision variable internal noise can be used, such as the following employed in a channelized Hotelling observer:

$$\lambda = \lambda_0 + \alpha \cdot x \quad (6);$$

where $\lambda$ is the final DL-MO test statistics, a is a constant weighting factor, and $x \in N$, $0, \text{std}(\lambda_{0,bkg})^2$ denotes a normal random variable with zero expectation and a variance equal to that of PLS-DA test statistics for lesion-absent cases (denoted as $\lambda_{0,bkg}$). The value of $\alpha$ can be determined by calibrating DL-MO performance and HO performance at one preselected experimental condition. After calibration, the same value of a can be used in the other conditions.

The proposed DL-MO method can be used in many clinical tasks, including detection, classification, and localization. Here, an example for a lesion-localization task is described. For the lesion-localization task, a simple nodule-searching process can be incorporated. A sliding window can be applied to generate voxel-wise test statistics of DL-MO (termed as a "Heat map"). The voxel that yields the maximal $\lambda$ (e.g., max $\lambda_i$ for i∈ROI) can be considered as the most likely center of a lesion (e.g., a lung nodule). The area under localization receiver-operating-characteristics curve (AUC_LROC) can be employed as the figure-of-merit ("FOM") of the DL-MO performance. The DL-MO can be trained and tested using independent datasets. Training data can include, for example, small image patches that are randomly extracted from patient images, while the testing dataset can use full field-of-view CT images.

In an example study, image data were prepared for comparing DL-MO and HO at different experimental conditions with varying lesion attributes (i.e., size and contrast), radiation dose, and image reconstruction types. The procedure of data preparation is summarized as follows.

Routine abdominal CT exams of seven adult patients were selected. The images were acquired using the same single-source 128 slice CT scanner. The images were lesion free. A validated noise insertion tool was used to simulate additional CT exams acquired with 50% and 25% of the routine radiation dose. Additionally or alternatively, the DL-NI system described in the present disclosure could be implemented as the noise insertion tool to simulate additional CT images.

To generate data for the MO and HO studies, volumetric CT images of a real liver metastatic lesion were numerically modified to create lesion models with four different sizes (5, 7, 9, and 11 mm) and three different contrast levels (15, 20, and 25 HU). These lesion models were inserted into multiple locations in normal patient liver images, using a previously validated projection-based method. Additionally or alternatively, lesion can be inserted using the DL-LI systems described in the present disclosure.

Projection data, with inserted noise and lesions, were reconstructed using a weighted filtered back projection algorithm (WFBP) and an iterative reconstruction algorithm-sinogram affirmed iterative reconstruction (IR: SAFIRE). When using the DL-NI and DL-LI tools described in the present disclosure, the noise and lesion insertion occurs in the image domain.

To improve the performance the DL-MO, several data augmentation strategies to augment the experimental trial images can be used, including image conversion, cropping, z-direction interpolation, and small angle rotation. Image conversion was used to convert the dynamic range of CT images to that of the natural images in ImageNet, while the other strategies were mainly used to increase the amount of training samples.

In image conversion, the original images were transformed to the grayscale of [0, 255] after applying an abdominal display window (WW/WL: 400/40 HU), that is, to make CT images more similar to the natural images in ImageNet. Specifically, the CT numbers were restricted to the dynamic range defined by the abdominal display window (i.e., [−160, 240] HU), and then were normalized to the range [0, 255]. The central three images of each VOI were retrieved to form a pseudo color image as the input of DL-MO, by stacking the three images as RGB channels. This was done because the ResNet-50 was pre-trained to classify the natural images with RGB channels. Thus, the first and the last images of each VOI were excluded from the training of DL-MO. Nevertheless, it is expected that these adjustments will not downgrade DL-MO performance, since the central three images already contained the most significant signal information.

As for cropping, additional multisized VOIs were cropped out of each VOI. The size of these VOIs uniformly ranged from 7.4×7.4 mm² to 52.0×52.0 mm² in the axial plane. These augmented VOIs were not resized to 224×224 pixels (i.e., the typical image size used in ImageNet), and thus, the dimension of the extracted CNN codes depended on the size of the input VOI. For instance, a VOI with 70×70×3 voxels (i.e., 52.0×52.0×9 mm³) would yield a CNN code with 5×5×256 features, at the 26th convolutional layer. So, zero padding was applied to each feature channel of the extracted CNN codes from smaller VOIs to ensure that all CNN codes had consistent dimension (i.e., 5×5×256 features per sample).

In z-direction interpolation, a voxel-wise interpolation along the z-direction was used to generate more VOIs (still with 3 mm slice increment). For small angle rotation, each VOI was rotated by a random angle from a uniform distribution within the range of [−5.0°, 5.0°], and a "nearest neighbor" interpolation method was used to generate the rotated images, to avoid significantly altering image texture. Together, these data augmentation strategies generated 9,424 additional lesion-present and lesion-absent trials for each experimental condition.

Figure 9:
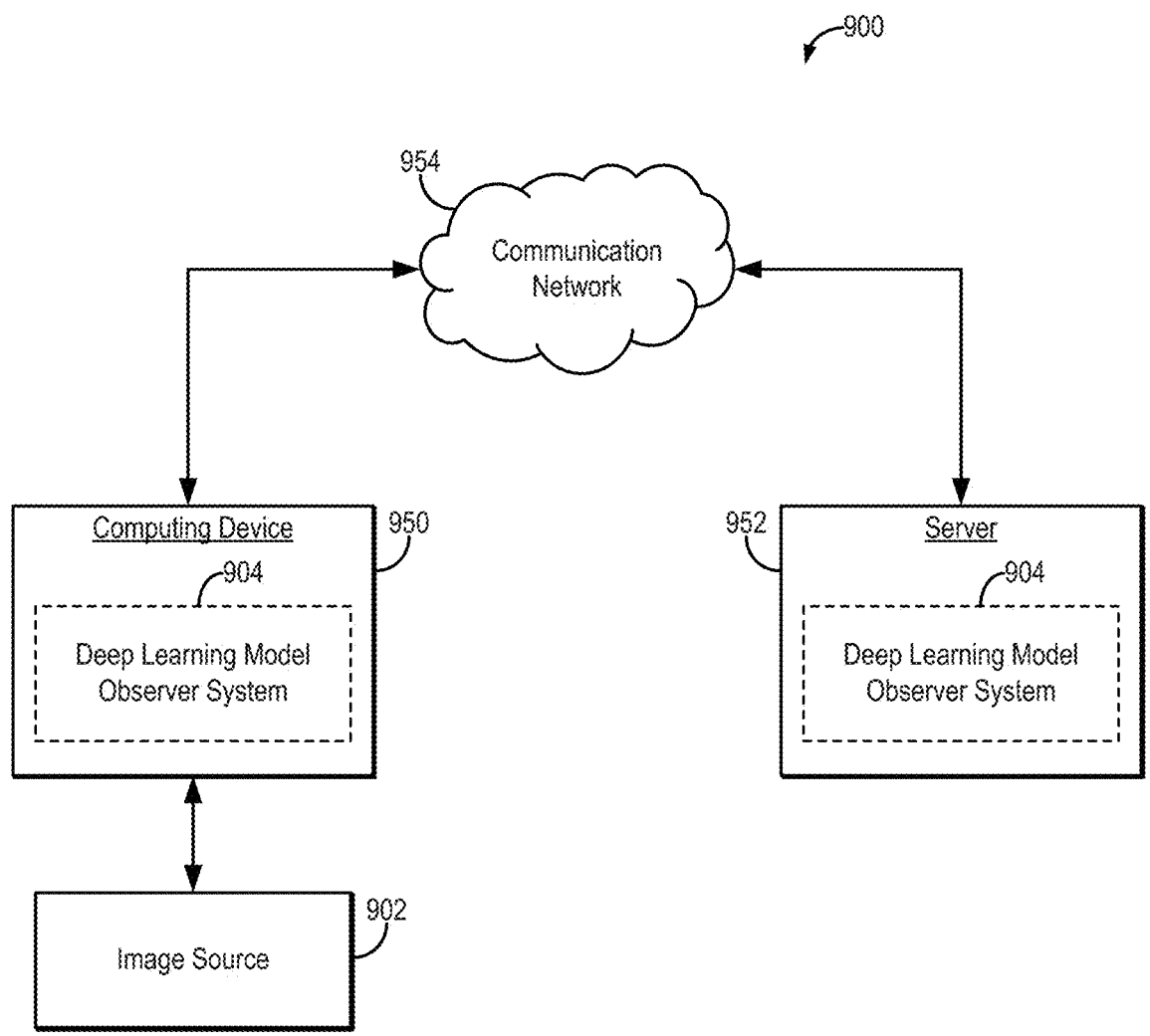
FIG. 9 is a block diagram of an example deep learning model observer system.

Referring now to FIG. 9, an example of a system 900 for image quality evaluation and virtual clinical trial using a deep learning-based model observer ("DL-MO") in accordance with some embodiments of the systems and methods described in the present disclosure is shown. As shown in FIG. 9, a computing device 950 can receive one or more types of data (e.g., CT image data) from image source 902, which may be a CT image source or other suitable medical image source. In some embodiments, computing device 950 can execute at least a portion of a deep learning model observer system 904 to implement image quality evaluation and a virtual clinical trial from data received from the image source 902.

Additionally or alternatively, in some embodiments, the computing device 950 can communicate information about data received from the image source 902 to a server 952 over a communication network 954, which can execute at least a portion of the deep learning model observer system 904. In such embodiments, the server 952 can return information to the computing device 950 (and/or any other suitable computing device) indicative of an output of the deep learning model observer system 904.

In some embodiments, computing device 950 and/or server 952 can be any suitable computing device or combination of devices, such as a desktop computer, a laptop computer, a smartphone, a tablet computer, a wearable computer, a server computer, a virtual machine being executed by a physical computing device, and so on. The computing device 950 and/or server 952 can also reconstruct images from the data.

In some embodiments, image source 902 can be any suitable source of image data (e.g., measurement data, images reconstructed from measurement data), such as a CT system (or other suitable medical imaging system), another computing device (e.g., a server storing image data), and so on. In some embodiments, image source 902 can be local to computing device 950. For example, image source 902 can be incorporated with computing device 950 (e.g., computing device 950 can be configured as part of a device for capturing, scanning, and/or storing images). As another example, image source 902 can be connected to computing device 950 by a cable, a direct wireless link, and so on. Additionally or alternatively, in some embodiments, image source 902 can be located locally and/or remotely from computing device 950, and can communicate data to computing device 950 (and/or server 952) via a communication network (e.g., communication network 954).

In some embodiments, communication network 954 can be any suitable communication network or combination of communication networks. For example, communication network 954 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 9 can each be any suitable communications link or combination of communications links, such as wired links, fiber optic links, Wi-Fi links, Bluetooth links, cellular links, and so on.

Figure 10:
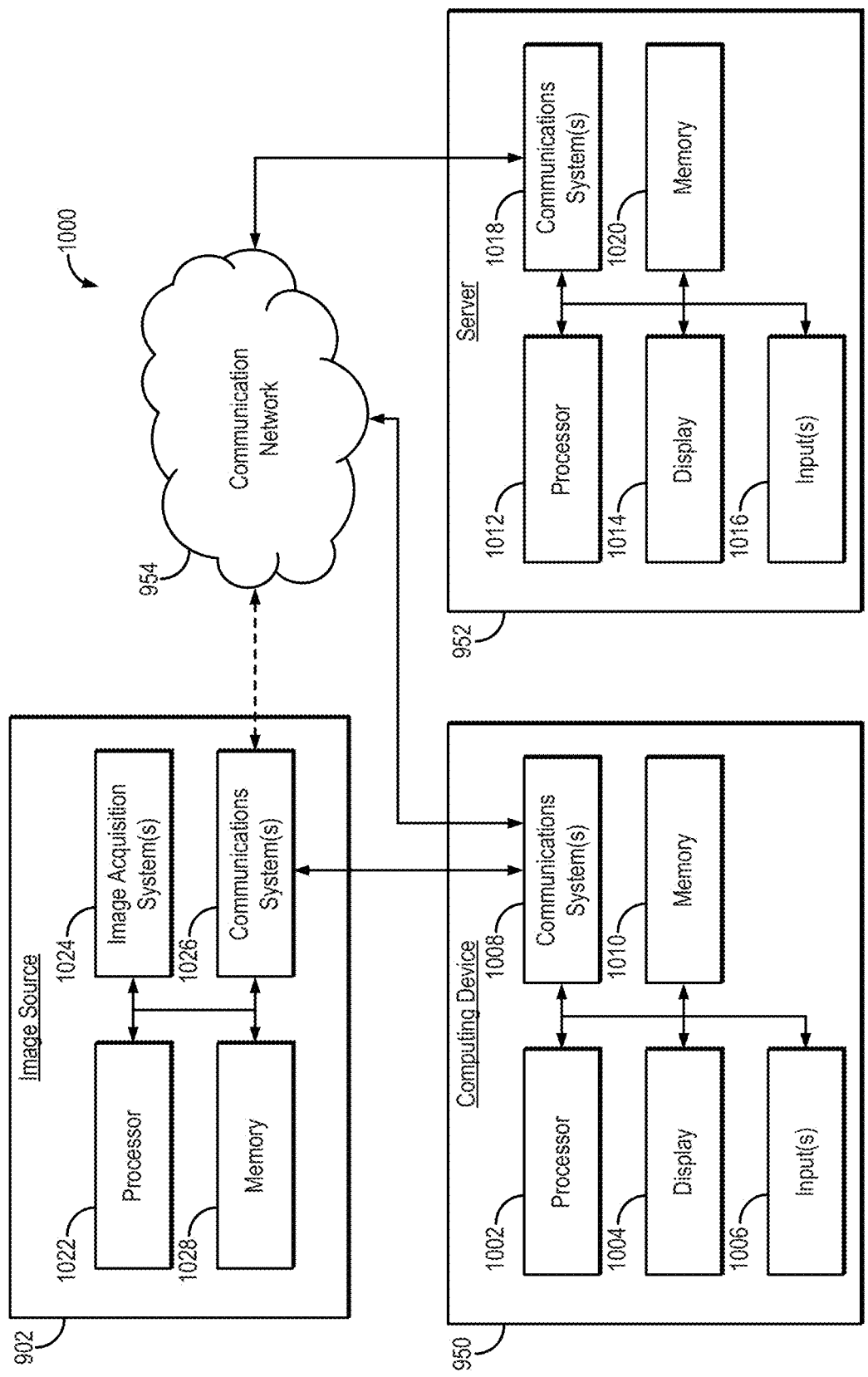
FIG. 10 is a block diagram of example components that can implement the deep learning model observer system of FIG. 9.

Referring now to FIG. 10, an example of hardware 1000 that can be used to implement image source 902, computing device 950, and server 952 in accordance with some embodiments of the systems and methods described in the present disclosure is shown. As shown in FIG. 10, in some embodiments, computing device 950 can include a processor 1002, a display 1004, one or more inputs 1006, one or more communication systems 1008, and/or memory 1010. In some embodiments, processor 1002 can be any suitable hardware processor or combination of processors, such as a central processing unit ("CPU"), a graphics processing unit ("GPU"), and so on. In some embodiments, display 1004 can include any suitable display devices, such as a computer monitor, a touchscreen, a television, and so on. In some embodiments, inputs 1006 can include any suitable input devices and/or sensors that can be used to receive user input, such as a keyboard, a mouse, a touchscreen, a microphone, and so on.

In some embodiments, communications systems 1008 can include any suitable hardware, firmware, and/or software for communicating information over communication network 954 and/or any other suitable communication networks. For example, communications systems 1008 can include one or more transceivers, one or more communication chips and/or chip sets, and so on. In a more particular example, communications systems 1008 can include hardware, firmware and/or software that can be used to establish a Wi-Fi connection, a Bluetooth connection, a cellular connection, an Ethernet connection, and so on.

In some embodiments, memory 1010 can include any suitable storage device or devices that can be used to store instructions, values, data, or the like, that can be used, for example, by processor 1002 to present content using display 1004, to communicate with server 952 via communications system(s) 1008, and so on. Memory 1010 can include any suitable volatile memory, non-volatile memory, storage, or any suitable combination thereof. For example, memory 1010 can include RAM, ROM, EEPROM, one or more flash drives, one or more hard disks, one or more solid state drives, one or more optical drives, and so on. In some embodiments, memory 1010 can have encoded thereon, or otherwise stored therein, a computer program for controlling operation of computing device 950. In such embodiments, processor 1002 can execute at least a portion of the computer program to present content (e.g., images, user interfaces, graphics, tables), receive content from server 952, transmit information to server 952, and so on.

In some embodiments, server 952 can include a processor 1012, a display 1014, one or more inputs 1016, one or more communications systems 1018, and/or memory 1020. In some embodiments, processor 1012 can be any suitable hardware processor or combination of processors, such as a CPU, a GPU, and so on. In some embodiments, display 1014 can include any suitable display devices, such as a computer monitor, a touchscreen, a television, and so on. In some embodiments, inputs 1016 can include any suitable input devices and/or sensors that can be used to receive user input, such as a keyboard, a mouse, a touchscreen, a microphone, and so on.

In some embodiments, communications systems 1018 can include any suitable hardware, firmware, and/or software for communicating information over communication network 954 and/or any other suitable communication networks. For example, communications systems 1018 can include one or more transceivers, one or more communication chips and/or chip sets, and so on. In a more particular example, communications systems 1018 can include hardware, firmware and/or software that can be used to establish a Wi-Fi connection, a Bluetooth connection, a cellular connection, an Ethernet connection, and so on.

In some embodiments, memory 1020 can include any suitable storage device or devices that can be used to store instructions, values, data, or the like, that can be used, for example, by processor 1012 to present content using display 1014, to communicate with one or more computing devices 950, and so on. Memory 1020 can include any suitable volatile memory, non-volatile memory, storage, or any suitable combination thereof. For example, memory 1020 can include RAM, ROM, EEPROM, one or more flash drives, one or more hard disks, one or more solid state drives, one or more optical drives, and so on. In some embodiments, memory 1020 can have encoded thereon a server program for controlling operation of server 952. In such embodiments, processor 1012 can execute at least a portion of the server program to transmit information and/or content (e.g., data, images, a user interface) to one or more computing devices 950, receive information and/or content from one or more computing devices 950, receive instructions from one or more devices (e.g., a personal computer, a laptop computer, a tablet computer, a smartphone), and so on.

In some embodiments, image source 902 can include a processor 1022, one or more image acquisition systems 1024, one or more communications systems 1026, and/or memory 1028. In some embodiments, processor 1022 can be any suitable hardware processor or combination of processors, such as a CPU, a GPU, and so on. In some embodiments, the one or more image acquisition systems 1024 are generally configured to acquire data, images, or both, and can include a CT system or other suitable medical imaging system. Additionally or alternatively, in some embodiments, one or more image acquisition systems 1024 can include any suitable hardware, firmware, and/or software for coupling to and/or controlling operations of a CT system or other suitable medical imaging system. In some embodiments, one or more portions of the one or more image acquisition systems 1024 can be removable and/or replaceable.

Note that, although not shown, image source 902 can include any suitable inputs and/or outputs. For example, image source 902 can include input devices and/or sensors that can be used to receive user input, such as a keyboard, a mouse, a touchscreen, a microphone, a trackpad, a trackball, and so on. As another example, image source 902 can include any suitable display devices, such as a computer monitor, a touchscreen, a television, etc., one or more speakers, and so on.

In some embodiments, communications systems 1026 can include any suitable hardware, firmware, and/or software for communicating information to computing device 950 (and, in some embodiments, over communication network 954 and/or any other suitable communication networks). For example, communications systems 1026 can include one or more transceivers, one or more communication chips and/or chip sets, and so on. In a more particular example, communications systems 1026 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 1028 can include any suitable storage device or devices that can be used to store instructions, values, data, or the like, that can be used, for example, by processor 1022 to control the one or more image acquisition systems 1024, and/or receive data from the one or more image acquisition systems 1024; to images from data; present content (e.g., images, a user interface) using a display; communicate with one or more computing devices 950; and so on. Memory 1028 can include any suitable volatile memory, non-volatile memory, storage, or any suitable combination thereof. For example, memory 1028 can include RAM, ROM, EEPROM, one or more flash drives, one or more hard disks, one or more solid state drives, one or more optical drives, and so on. In some embodiments, memory 1028 can have encoded thereon, or otherwise stored therein, a program for controlling operation of image source 902. In such embodiments, processor 1022 can execute at least a portion of the program to generate images, transmit information and/or content (e.g., data, images) to one or more computing devices 950, receive information and/or content from one or more computing devices 950, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

As noted above, the DL-MO system can take as inputs input image data that include routine CT images, lesion-present images, and multiple lower-dose CT images. In these instances, the DL-MO system describes above can be in communication with, or otherwise integrate, the DL-NI system of FIG. 3 and the DL-LI system of FIG. 6.

The present disclosure has described one or more preferred embodiments, and it should be appreciated that many equivalents, alternatives, variations, and modifications, aside from those expressly stated, are possible and within the scope of the invention.

The invention claimed is:

1. A method for generating a report indicating diagnostic performance of a computed tomography (CT) system, the method comprising:
   (a) accessing CT images acquired from a subject using a CT system, the CT images depicting anatomy of the subject;
   (b) generating lesion-present images by inserting lesion data to the CT images, the lesion-present images depicting lesions added to the anatomy of the subject;
   (c) generating lower-dose CT images by inserting noise to the CT images and the lesion-present images, the lower-dose CT images corresponding to lower dose representations of the CT images and lesion-present images;
   (d) generating one or more measures of diagnostic performance of the CT system by inputting input image data comprising the CT images, lesion-present images, and lower-dose CT images to a deep learning-based model observer, generating output as the one or more measures of diagnostic performance; and (e) generating a report of diagnostic performance of the CT system based on the one or more measures of diagnostic performance of the CT system.

2. The method as recited in claim 1, wherein the deep learning model observer comprises a pre-trained convolutional neural network (CNN), a feature engineering model, and an internal noise component, wherein:
the input image data are input to the pre-trained CNN, generating output as CNN codes;
the CNN codes output from the pre-trained CNN are input to the feature engineering model, generating output as test statistics data; and
the test statistics data output from the feature engineering model are input to the internal noise component, generating output as the one or more diagnostic performance measures.

3. The method as recited in claim 2, wherein the pre-trained CNN implements a residual CNN.

4. The method as recited in claim 2, wherein the feature engineering model implements a partial least square regression.

5. The method as recited in claim 4, wherein the partial least squares regression implements a partial least squares discriminant analysis model.

6. The method as recited in claim 1, wherein the lesion-present images are generated by inputting the CT image to a deep learning-based lesion insertion model, generating output as the lesion-present images.

7. The method as recited in claim 6, wherein the deep learning-based lesion insertion model implements a deep convolutional neural network architecture that is trained to insert lesions into different locations of the CT images by fusing multi-scaled features of patient lesion models with anatomical background in the CT images.

8. The method as recited in claim 1, wherein the lower-dose images are generated by inputting the CT images and the lesion-present images to a deep learning-based noise insertion model, generating output as the lower-dose CT images.

9. The method as recited in claim 8, wherein the deep learning-based noise insertion model implements an objective function having a perceptual loss function, a frequency-spectrum loss function, and a diversity loss function.

10. The method as recited in claim 9, wherein the perceptual loss function is configured to achieve perceptually-realistic low-dose CT images.

11. The method as recited in claim 9, wherein the frequency-spectrum loss function is configured to quantitatively match noise frequency components.

12. The method as recited in claim 9, wherein the diversity loss function is configured to provide sufficient diversity of noise realization.

13. The method as recited in claim 9, wherein the deep learning-based noise insertion model implements a neural network architecture containing a hybrid of local and non-local operators to model noise correlation in the CT images.

14. The method as recited in claim 13, wherein the neural network architecture implements functional modules that concatenate non-local operators and multi-scale local convolutional operators to model the noise correlation in the CT images.

15. The method as recited in claim 14, wherein the non-local operators comprise two-dimensional discrete cosine transformations.

16. The method as recited in claim 1, wherein at least some of the CT images contained in the input image data comprise lesion-absent images in which no lesions are present.

17. A method for generating lower dose computed tomography (CT) images, the method comprising:
(a) accessing with a computer system, CT images acquired from a subject using a CT system, the CT images depicting anatomy of the subject;
(b) generating lower-dose CT images by inserting noise to the CT images using the computer system, the lower-dose CT images corresponding to lower dose representations of the CT images; and
wherein the lower-dose images are generated with the computer system by inputting the CT images to a deep learning-based noise insertion model, generating output as the lower-dose CT images, wherein the deep learning-based noise insertion model implements an objective function having a perceptual loss function, a frequency-spectrum loss function, and a diversity loss function.

18. The method as recited in claim 17, wherein the perceptual loss function is configured to achieve perceptually-realistic low-dose CT images.

19. The method as recited in claim 17, wherein the frequency-spectrum loss function is configured to quantitatively match noise frequency components.

20. The method as recited in claim 17, wherein the diversity loss function is configured to provide sufficient diversity of noise realization.

21. The method as recited in claim 17, wherein the deep learning-based noise insertion model implements a neural network architecture containing a hybrid of local and non-local operators to model noise correlation in the CT images.

22. The method as recited in claim 21, wherein the neural network architecture implements functional modules that concatenate non-local operators and multi-scale local convolutional operators to model the noise correlation in the CT images.

23. The method as recited in claim 22, wherein the non-local operators comprise two-dimensional discrete cosine transformations.

24. A method for generating lesion-present images from computed tomography (CT) images, the method comprising:
(a) accessing with a computer system, CT images acquired from a subject using a CT system, the CT images depicting anatomy of the subject;
(b) generating lesion-present images by inserting lesion data to the CT images using the computer system, the lesion-present images depicting lesions added to the anatomy of the subject; and
wherein the lesion-present images are generated with the computer system by inputting the CT image to a deep learning-based lesion insertion model, generating output as the lesion-present images, wherein the deep learning-based lesion insertion model implements a deep convolutional neural network architecture that is trained to insert lesions into different locations of the CT images by fusing multi-scaled features of patient lesion models with anatomical background in the CT images.

* * * * *